United States Patent [19]

Kist

[11] Patent Number: 4,700,713

[45] Date of Patent: Oct. 20, 1987

[54] DEVICE FOR OBTAINING A SMEAR SAMPLE FROM A BODY CAVITY

[75] Inventor: Joost Kist, Amsterdam, Netherlands

[73] Assignee: Futura Nova B.V., Amsterdam, Netherlands

[21] Appl. No.: 947,827

[22] Filed: Dec. 30, 1986

[30] Foreign Application Priority Data

Dec. 31, 1985 [NL] Netherlands .......................... 8503596

[51] Int. Cl.⁴ ............................................. A61B 10/00
[52] U.S. Cl. ................................... 128/756; 128/757; 128/357; 15/159 A
[58] Field of Search ............... 128/357, 749, 751, 756, 128/757, 304, 310; 15/159 A

[56] References Cited

U.S. PATENT DOCUMENTS 3,881,464 5/1975 Levene ................................ 128/756
4,127,113 11/1978 Nollan ................................ 128/756

Primary Examiner—William E. Kamm
Assistant Examiner—Randy Citrin
Attorney, Agent, or Firm—Wolf, Greenfield & Sacks

[57] ABSTRACT

In a device for obtaining a smear sample from a body cavity, in particular the uterus mouth or cervix, a plurality of substantially parallel flexible bristles (3) is connected to a carrier (2) provided at one end of a stem (1). In order to ensure that cells from all the portions of the body cavity are sampled the bristles (3) extend substantially parallel to the stem (1) and the bristles (3) each have at least one longitudinal sharp edge (6). The said sharp edge (6) is adapted to scrape cells from the body cavity when the device is rotated about the stem axis.

13 Claims, 4 Drawing Figures

DEVICE FOR OBTAINING A SMEAR SAMPLE FROM A BODY CAVITY

The invention relates to a device for obtaining a smear sample from a body cavity, in particular the uterus mouth or cervix, comprising a plurality of substantially parallel flexible bristles connected to a carrier provided at one end of a stem.

BACKGROUND OF THE INVENTION

Such a device is known from the U.S. Pat. No. 4,127,113. Herein the carrier extends parallel to the stem and the bristles are directed substantially perpendicular to the stem. The carrier, when obtaining a smear sample, is placed with the bristles in the cervical canal and is rotated, whereby the ends of the bristles scrape the wall of the cervical canal. When the carrier is fully inserted in the cervical canal, an edge of a flattened blade at the end of the stem scrapes along the mouth of the cervix to remove cells therefrom.

In the pap smear test it is important for a proper diagnosis, that both squamo epithelial cells of the portio and cilindrical epithelial cells of the endocervical canal are present in the specimen to be examined (a so-called representative smear sample). This ensures, that the area of junction between ecto- and endocervix, i.e. the squamocolumnar junction, where the cervical carninoma and its early stages preferably develop, has been sampled in the cell collection, whereby a greater chance exists that the carcinoma or its early stages are discovered in time.

However, the known device has the disadvantage, that although cells from the cervical canal are removed in a reliable manner, cells from the junction area or the squamo area may be missed. This can for instance occur, when it is not possible to place the whole carrier with its bristles in the cervical canal, whereby the edge of the flattened blade does not scrape along the mouth of the cervix and no cells are removed from that place. In this way it is not possible to obtain a reliable illustration of the condition of the cervix.

A further disadvantage of the known device is, that when the cellular material removed from the cervix is delivered to the microscopic slide, the edge of the flattened blade serves as guide and the cellular material collected thereon does not arrive onto the slide.

SUMMARY OF THE INVENTION

It is an object of the present invention to provide a device for obtaining a smear sample from a body cavity, in particular the cervix, wherein the above mentioned disadvantages are removed in an effective way.

For this purpose the device according to the invention is characterized in that the bristles extend substantially parallel to the stem and the bristles each have at least one longitudinal sharp edge, with which it is enabled to scrape cells from the body cavity when rotating the device about the stem axis.

By means of this device it is possible to obtain a representative smear sample at all times, because some of the bristles, for instance those in the area of the extension of the stem are able to penetrate into the cervical canal and to scrape cells from the wall thereof, while the remaining bristles are able to scrape over a large area along the cervix.

In a favourable embodiment of the device according to the invention the free ends of the bristles in the area of the extension of the stem of the device protrude beyond those of the bristles disposed outwardly of this area.

Consequently the bristles in the area of the extension of the stem are adapted to penetrate even deeper into the cervical canal.

Furthermore, it is advantageously, when the bristles disposed in the area of the extension of the stem of the device are larger in cross section than the remaining bristles.

In this way it is simplified to insert the bristles in the area of the extension of the stem into the cervical canal, and said bristles are able to serve as an axis of rotation for the device.

A preferred embodiment of the device according to the invention is characterized in that the carrier at the side facing the bristles has a curved configuration which is adapted to the shape of the mouth of the body cavity.

In this way a removal of cells in a large area of the mouth of the cervix and the cervical canal is obtained, and the bristles in the area of the extension of the stem of the device are properly supported.

In a favourable embodiment of the device according to the invention the carrier has an elastic construction.

This promotes that the outer bristles are spread out, whereby it is made possible for the bristles to cover a large area of the mouth of the cervix.

An advantageous embodiment of the device according to the invention is characterized in that the bristles are substantially half round in transverse section.

Consequently a bristle having a sharp edge is obtained in a very simple way, which enables the cellular material to be collected onto the non-curved portion of each hair when the smear sample is obtained.

In one embodiment of the device the carrier with the bristles is substantially symmetrical with respect to a longitudinal plane extending through the stem axis.

In an alternative embodiment the carrier at one side of a longitudinal plane extending through the stem axis terminates shorter than at the other side.

This embodiment is in particular advantageously when the device is used with very small vaginas, as the transverse size of the device is minimized so that the access to the cervical canal is easier.

The invention will hereafter be elucidated with reference to the drawing, which shows an embodiment of the device for obtaining a smear sample according to the invention by way of example.

DESCRIPTION OF THE PREFERRED EMBODIMENTS

Figure 1:
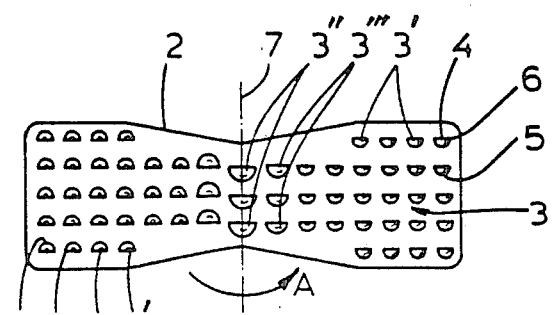
FIG. 1 schematically illustrates the use of a device for obtaining a smear sample according to the invention.
Figure 2:
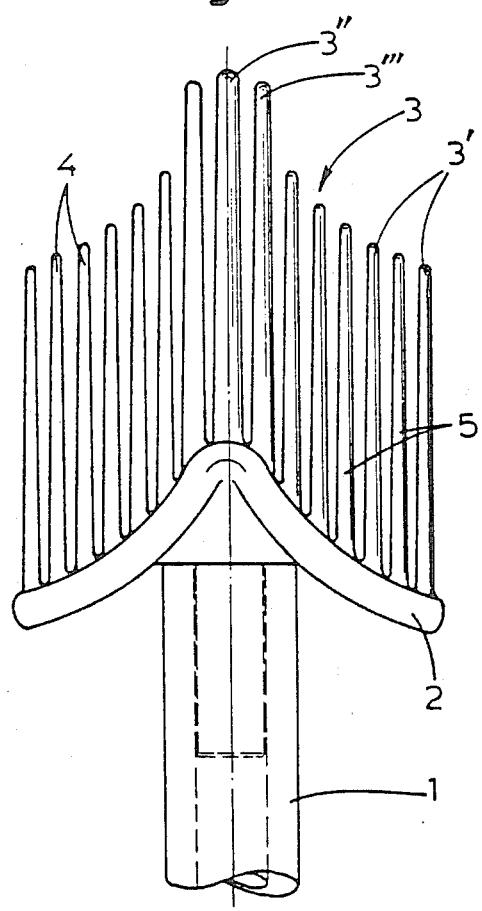
FIG. 2 shows a part of the device of FIG. 1, on an enlarged scale.

The drawing shows an embodiment of a device for obtaining a smear sample from a body cavity, in particular the uterus mouth or cervix 9. This device comprises a stem 1 having a circular transverse section, one end thereof being provided with a carrier 2, which carries a plurality of bristles 3 extending parallel to the stem 1, so that there is formed a brush. The bristles 3 will be described in detail further on.

Figure 3:
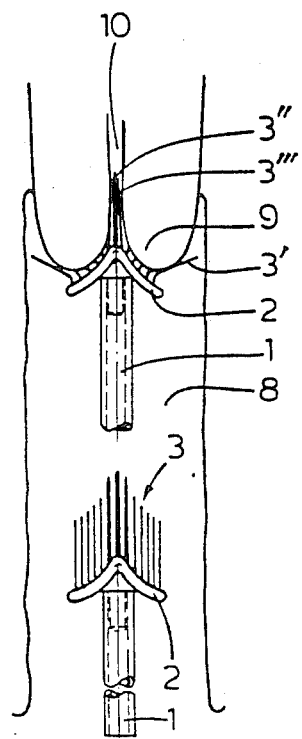
FIG. 3 is an upper view of the device of FIG. 2.

The bristles 3 distributed over the surface of the carrier 2 have a half round transverse section with a flat side 4 and a round portion 5, as can be clearly seen in FIG. 3. As a result of this configuration of the bristles 3 a sharp edge 6 is obtained at the junction between the flat side 4 and the round portion 5 of each hair 3. By this measure the sharp edges 6 at the side of the hairs 3 facing away from the line of extension of the stem of the device exert a scraping action onto the cellular wall of the cervix, when the device is rotated about the stem 1, so that cells will collect on the flat sides 4 of the bristles 3.

At one side of a longitudinal plane 7 extending through the stem 1 the flat sides 4 of the bristles 3 are directed to one long side of the carrier 2, and at the other side of this longitudinal plane 7 the flat sides 4 face the opposite long side of the carrier 2.

As a result cells will be scraped from the cellular wall only when the device is rotated about the stem 1 in the direction of the arrow A.

Of course it is possible to use hairs having other transverse sections, like rectangular or lenticular configurations.

The carrier 2 has a narrow construction when viewed in the longitudinal direction of the device, so that the sight onto the cervical canal is not hindered by the carrier 2 when the device is inserted into the cervical canal. Furthermore, the surface of the carrier 2 onto which the bristles 3 are provided has a curved configuration running the length thereof, the top of the curve being located in the transverse centre of the device and being adapted to the sectional configuration of the mouth of the cervix 9. The ends of the bristles 3 follow substantially the same curve as the carrier 2.

The device comprises three types of bristles 3, that is the bristles 3' located outwardly of the transverse centre of the carrier 2, the bristles 3" provided in the longitudinal plane 7 in the centre of the carrier 2 and the bristles 3''' at both sides of the row of bristles 3". The bristles 3" and 3''' are somewhat longer than the bristles 3', so that they project forwardly.

The projecting bristles 3" and 3''' located in the area of the transverse centre of the device fit into the cervical canal, in this way forming an axis of rotation for the device. In order to further increase this effect, the centre bristles 3" have a larger cross-section than the bristles 3', while the size of the cross-section of the bristles 3''' lies between that of the bristles 3' and 3". Consequently the bristles 3" and 3''' will penetrate deep into the cervical canal in an easier way (see FIG. 1). The top of the carrier 2 projecting in the centre thereby renders a proper support for the bristles 3" and 3'''.

The carrier 2 is slightly elastic, so that in use both free ends thereof bend slightly inwardly, wherein the roots of the bristles 3' in the neighboorhoud of the ends of the carrier 2 are directed outwardly. This promotes the spreading out of the bristles 3 over a large area of the mouth of the cervix 9 (see FIG. 1).

FIG. 1 schematically illustrates that the device is introduced into a vagina 8 and is disposed onto and partially into the mouth of the cervix 9. The bristles 3" and 3''' of the device penetrate into the cervical canal 10, while the remaining bristles 3' spread out over the surface of the mouth of the cervix. Because the bristles 3' located outwardly of the transverse centre bend as a consequence of the pressure exerted by the device onto the cervix in the longitudinal direction of the device, the centre bristles 3" and 3''' penetrate even deeper into the cervical canal 10.

When the device is introduced to the right place it is rotated for one or more revolutions about the stem axis in the scraping direction (arrow A), during which cellular material is collected on the flat sides 4 of the bristles 3', 3" and 3''', whereafter the device can be removed from the vagina 8.

After a smear sample has been taken from the cervix, the device is wiped two times, one time with each flat side, across a microscopic slide, whereby a convenient delivery of cellular material to the slide occurs as a result of the parallel position of the bristles 3.

The invention is not restricted to the embodiment shown in the drawing by way of example, which can be varied in different ways within the scope of the invention.

Figure 4:
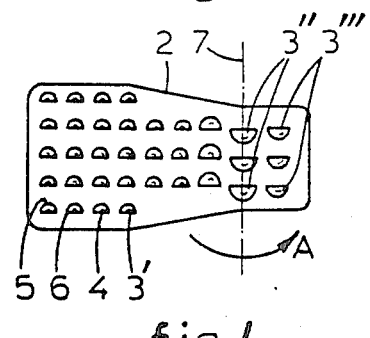
FIG. 4 is an upper view of an alternative embodiment according to the invention.

It is for instance possible to construct the carrier 2 such that the carrier is lower at one side of the stem 1 than at the other side of the stem (FIG. 4) short side of the carrier 2 may terminate after the row of bristles 3'''. This embodiment is in particular advantageously for use in very small vaginas.

I claim:

1. A device for obtaining a smear sample from a body cavity, in particular the uterus mouth or cervix, comprising
an elongated stem;
a carrier at one end of the stem;
a plurality of bristles projecting from the carrier and extending substantially parallel to the stem the bristles each having at least one longitudinal sharp edge, adapted to scrape cells from the body cavity when the device is rotated about the stem axis.

2. A device as claimed in claim 1, wherein free ends of the bristles in the area remote from the carrier adjacent the longitudinal axis of the stem of the device protrude beyond.

3. A device as claimed in claim 1, wherein the bristles disposed in the area adjacent the longitudinal axis of the stem of the device have a larger cross-section than the remaining bristles.

4. A device as claimed in one of the claims 1, wherein the carrier at the side facing the bristles has a curved configuration which is adapted to the shape of the mouth of the body cavity.

5. A device as claimed in claim 4, wherein the bristles disposed outwardly of the center have substantially the same length as each other.

6. A device as claimed in claim 1, wherein the carrier has an elastic construction.

7. A device as claimed in claim 1, wherein the carrier has a narrow configuration when viewed in longitudinal direction of the stem.

8. A device as claimed in claim 1, wherein the sharp edge of the bristles are directed such that the bristles are adapted to exert a scraping action in only one direction of rotation of the device.

9. A device as claimed in claim 7, wherein the bristles at one side of a longitudinal plane extending through the stem axis are rotated 180° about their longitudinal axis with respect to the bristles at the other side of the longitudinal plane.

10. A device as claimed in claim 1, wherein the bristles are substantially half round in transverse section.

11. A device as claimed in claim 1, wherein each bristle has one flat longitudinal side.

12. A device as claimed in claim 1, wherein the carrier with the bristles is substantially symmetrical with respect to a longitudinal plane extending through the stem axis.

13. A device as claimed in claim 1, wherein the carrier at one side of a longitudinal plane extending through the stem axis terminates shorter than at the other side.

* * * * *

UNITED STATES PATENT AND TRADEMARK OFFICE
CERTIFICATE OF CORRECTION

PATENT NO. : 4,700,713

DATED : October 20, 1987

INVENTOR(S) : Joost Kist

It is certified that error appears in the above-identified patent and that said Letters Patent is hereby corrected as shown below:

In column 4, line 30, delete "in the area" after bristles and insert --in the area-- after carrier; column 4, line 32, insert --the remaining bristles-- after beyond.

Signed and Sealed this

Seventh Day of August, 1990

Attest:

HARRY F. MANBECK, JR.

*Attesting Officer*   Commissioner of Patents and Trademarks